US012066325B2

(12) United States Patent
Donovan

(10) Patent No.: US 12,066,325 B2
(45) Date of Patent: Aug. 20, 2024

(54) POWER METER SYSTEMS FOR ADDITIVE MANUFACTURING MACHINES

(71) Applicant: Collins Engine Nozzles, Inc., Des Moines, IA (US)

(72) Inventor: Matthew Donovan, Ankeny, IA (US)

(73) Assignee: Collins Engine Nozzles, Inc., Des Moines, IA (US)

( * ) Notice: Subject to any disclaimer, the term of this patent is extended or adjusted under 35 U.S.C. 154(b) by 1681 days.

(21) Appl. No.: 15/632,141

(22) Filed: Jun. 23, 2017

(65) Prior Publication Data

US 2018/0369913 A1    Dec. 27, 2018

(51) Int. Cl.
| | |
|---|---|
| *B22F 3/105* | (2006.01) |
| *A61N 5/01* | (2006.01) |
| *B22F 10/28* | (2021.01) |
| *B22F 10/36* | (2021.01) |
| *B22F 12/20* | (2021.01) |
| *B23K 15/00* | (2006.01) |
| *B23K 15/10* | (2006.01) |
| *B23K 26/08* | (2014.01) |
| *B29C 64/386* | (2017.01) |

(Continued)

(52) U.S. Cl.
CPC .............. *G01J 1/4257* (2013.01); *A61N 5/01* (2013.01); *B22F 10/28* (2021.01); *B22F 10/36* (2021.01); *B22F 12/20* (2021.01); *B23K 15/0086* (2013.01); *B23K 15/10* (2013.01); *B23K 26/08* (2013.01); *B29C 64/386* (2017.08); *G01J 1/0219* (2013.01); *G01J 1/0252* (2013.01); *G01J 1/0271* (2013.01); *G21K 5/10* (2013.01); *B33Y 30/00* (2014.12); *B33Y 50/02* (2014.12)

(58) Field of Classification Search
CPC ..... B22F 3/1055; G01J 1/0271; G01J 1/0219; G01J 1/4257; G01J 1/0252; G21K 5/10; B23K 26/08; B23K 15/10; A61N 5/01
See application file for complete search history.

(56) References Cited

U.S. PATENT DOCUMENTS

| | | | |
|---|---|---|---|
| 9,586,298 B2 | 3/2017 | Jones et al. | |
| 2003/0033706 A1* | 2/2003 | Sekino | G03B 17/26 29/432 |

(Continued)

FOREIGN PATENT DOCUMENTS

| | | |
|---|---|---|
| DE | 102015007790 A1 | 12/2016 |
| EP | 3210713 A1 | 8/2017 |

OTHER PUBLICATIONS

Extended European Search Report of the European Patent Office, dated Oct. 23, 2018, issued in corresponding European Patent Application No. 18178619.5.

*Primary Examiner* — Andrew Schechter
*Assistant Examiner* — Jeremy A Delozier
(74) *Attorney, Agent, or Firm* — Bachman & LaPointe, P.C.

(57) ABSTRACT

A contained radiation power metering system for measuring power of a radiation source of an additive manufacturing machine includes a base configured to fit within the additive manufacturing machine, a radiation sensor connected to the base and configured to receive radiation from the radiation source and output a radiation power signal, and a wireless module disposed on the base configured to receive the radiation power signal and transmit the radiation power signal from the system to a separate wireless receiver.

20 Claims, 3 Drawing Sheets

(51) Int. Cl.
G01J 1/02 (2006.01)
G01J 1/42 (2006.01)
G21K 5/10 (2006.01)
*B33Y 30/00* (2015.01)
*B33Y 50/02* (2015.01)

(56) References Cited

U.S. PATENT DOCUMENTS

| | | | | |
|---|---|---|---|---|
| 2011/0005282 A1* | 1/2011 | Powers | ............... | E05B 81/10 |
| | | | | 70/63 |
| 2016/0280734 A1* | 9/2016 | Moore | ............... | B01J 14/00 |
| 2016/0318113 A1 | 11/2016 | Enyedy et al. | | |
| 2017/0068266 A1 | 3/2017 | Enyedy | | |
| 2017/0242424 A1* | 8/2017 | Spears | ............... | B29C 64/393 |
| 2017/0331172 A1* | 11/2017 | Puchades | ............ | H01Q 1/2208 |

\* cited by examiner

POWER METER SYSTEMS FOR ADDITIVE MANUFACTURING MACHINES

BACKGROUND

1. Field

The present disclosure relates to additive manufacturing, more specifically to power meter systems for additive manufacturing machines.

2. Description of Related Art

Laser based powder bed fusion additive manufacturing systems require precise use of the energy source. As such, these systems require frequent verification of the laser power, using some form of laser power meter. Traditional power meters are awkward to use and often involve bypassing of interlock systems of the machine to measure the laser power. Additionally, these meters require an external power source which requires using external cables. External liquid cooling lines can also be required. These external connections violate the inert integrity of a metal sintering system and contaminate the feedstock by exposure to oxygen.

Such conventional methods and systems have generally been considered satisfactory for their intended purpose. However, there is still a need in the art for improved power meter systems. The present disclosure provides a solution for this need.

SUMMARY

In accordance with at least one aspect of this disclosure, a contained radiation power metering system for measuring power of a radiation source of an additive manufacturing machine includes a base configured to fit within the additive manufacturing machine, a radiation sensor connected to the base and configured to receive radiation from the radiation source and output a radiation power signal, and a wireless module disposed on the base configured to receive the radiation power signal and transmit the radiation power signal from the system to a separate wireless receiver.

The system can include an input adapter operatively connected to the radiation sensor to receive the radiation power signal for converting the radiation power signal from a first format to second format operable with the wireless module. A battery can be disposed on the base and can be in electrical communication with the wireless module and/or the radiation sensor (if it requires power for example).

The base can be a cartridge plate and can be configured to removably fit onto a build plate mount in the additive manufacturing machine. The radiation sensor can be mounted to the base on a post and is positioned relative to the base for focal length and centering position of the radiation source.

In certain embodiments, the system can include a cooling system (e.g., liquid cooling system) operatively connected to the radiation sensor to cool the radiation sensor. The cooling system can include a coolant tank mounted to the base.

The cooling system can include a pump configured to pump coolant to the radiation sensor. The radiation sensor can be fluidly connected to the coolant tank via one or more coolant lines. The one or more coolant lines can include a pump line and a return line. In certain embodiments, the radiation sensor can include a housing with an internal volume configured to receive coolant.

In certain embodiments, the base can be configured to fit between a build plate and a powder bed of an additive manufacturing system and is configured to bolt to the additive manufacturing machine. The radiation sensor can be a laser power sensor and/or any other suitable sensor for any suitable radiation source.

In accordance with at least one aspect of this disclosure, a method for measuring the power of a radiation source of an additive manufacturing machine can include inserting a contained radiation power metering system into the machine, sealing the contained radiation power metering system in the machine, irradiating a radiation sensor of the contained radiation power metering system with the radiation source, and transmitting a wireless signal from the contained radiation power metering system within the machine to provide a reading of power of the radiation source. The additive manufacturing machine can be a powder bed fusion machine or any other suitable additive manufacturing machine.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
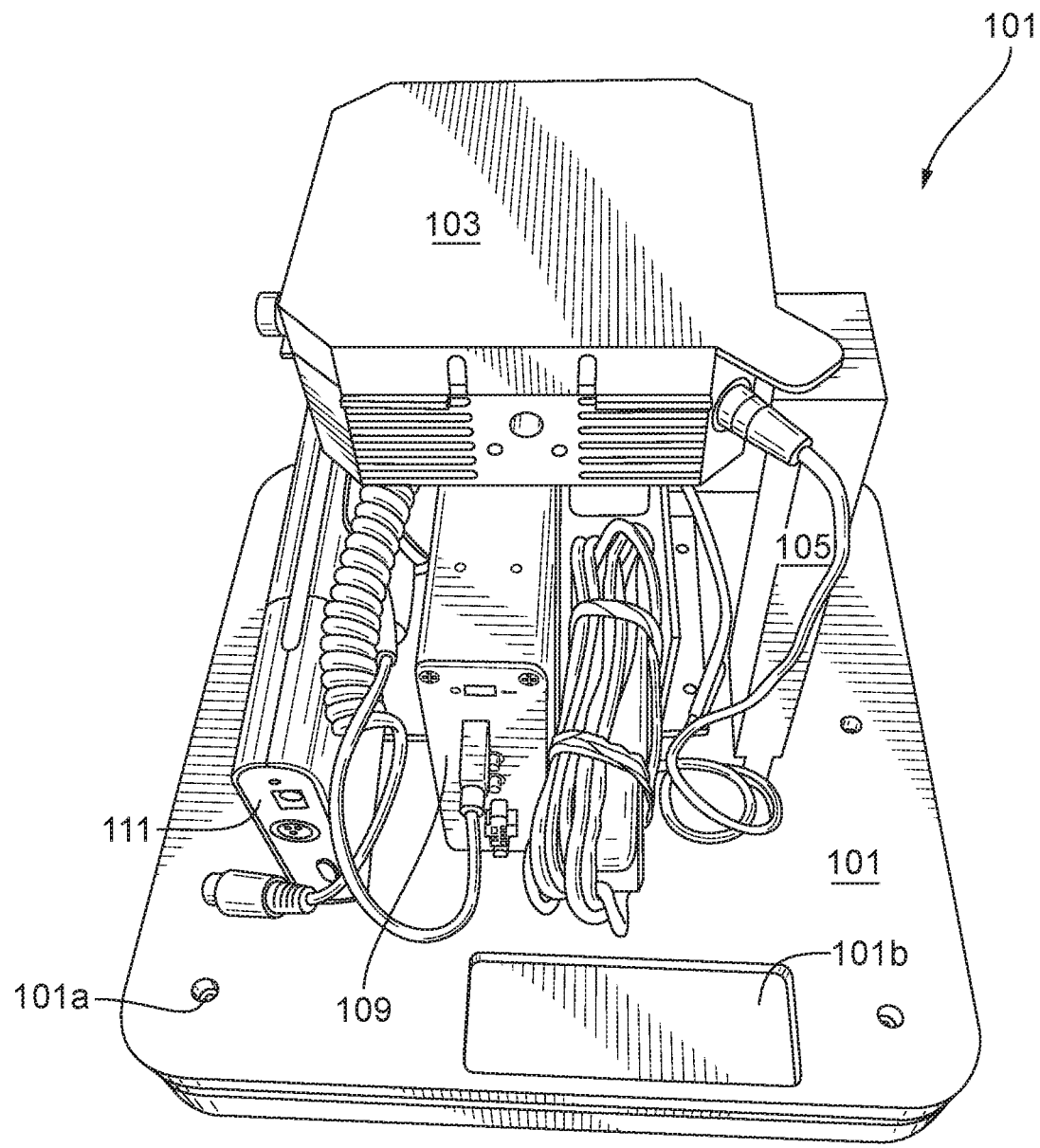
FIG. 1 is a perspective view of an embodiment of a system in accordance with this disclosure.
Figure 2:
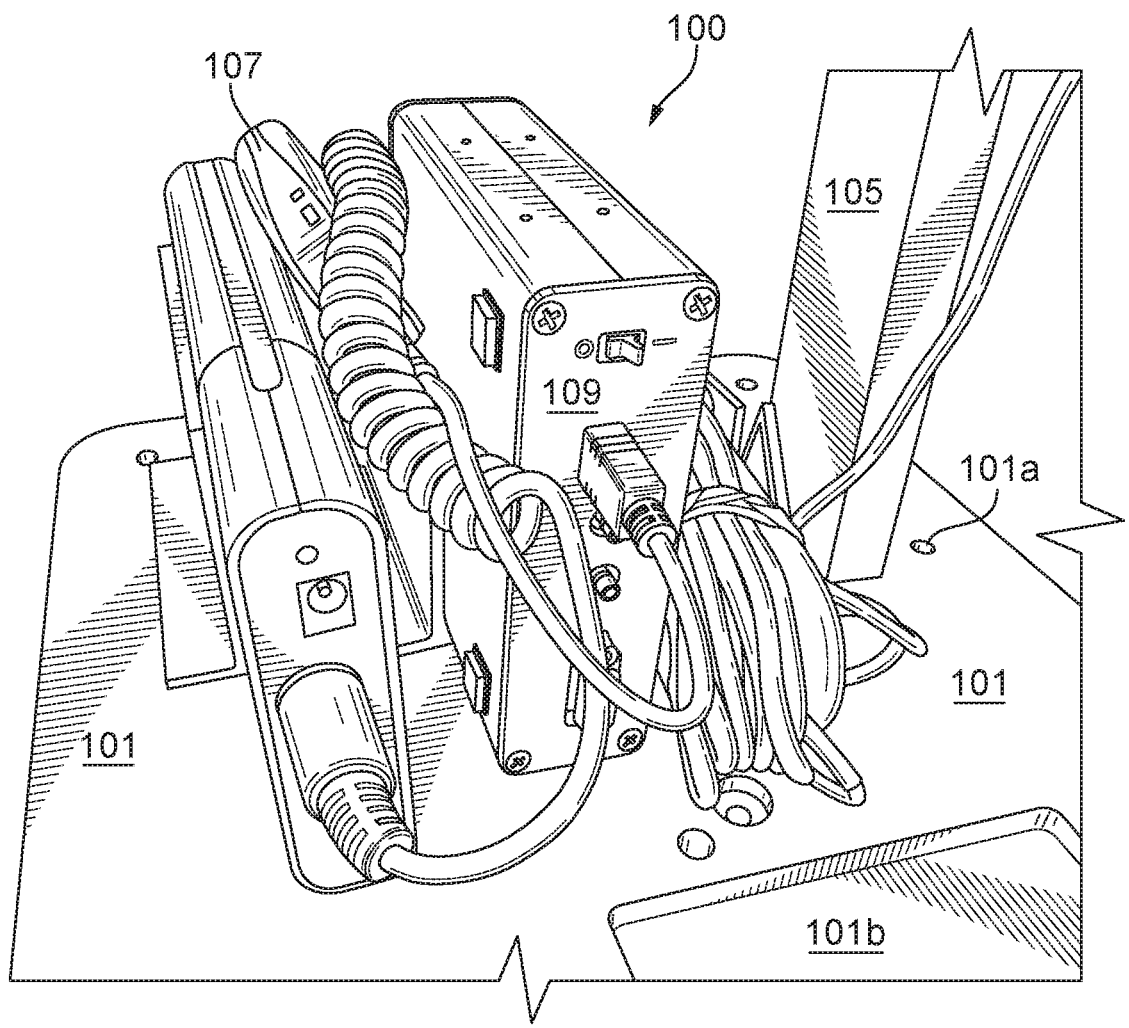
FIG. 2 is another perspective view of the embodiment of FIG. 1.
Figure 3:
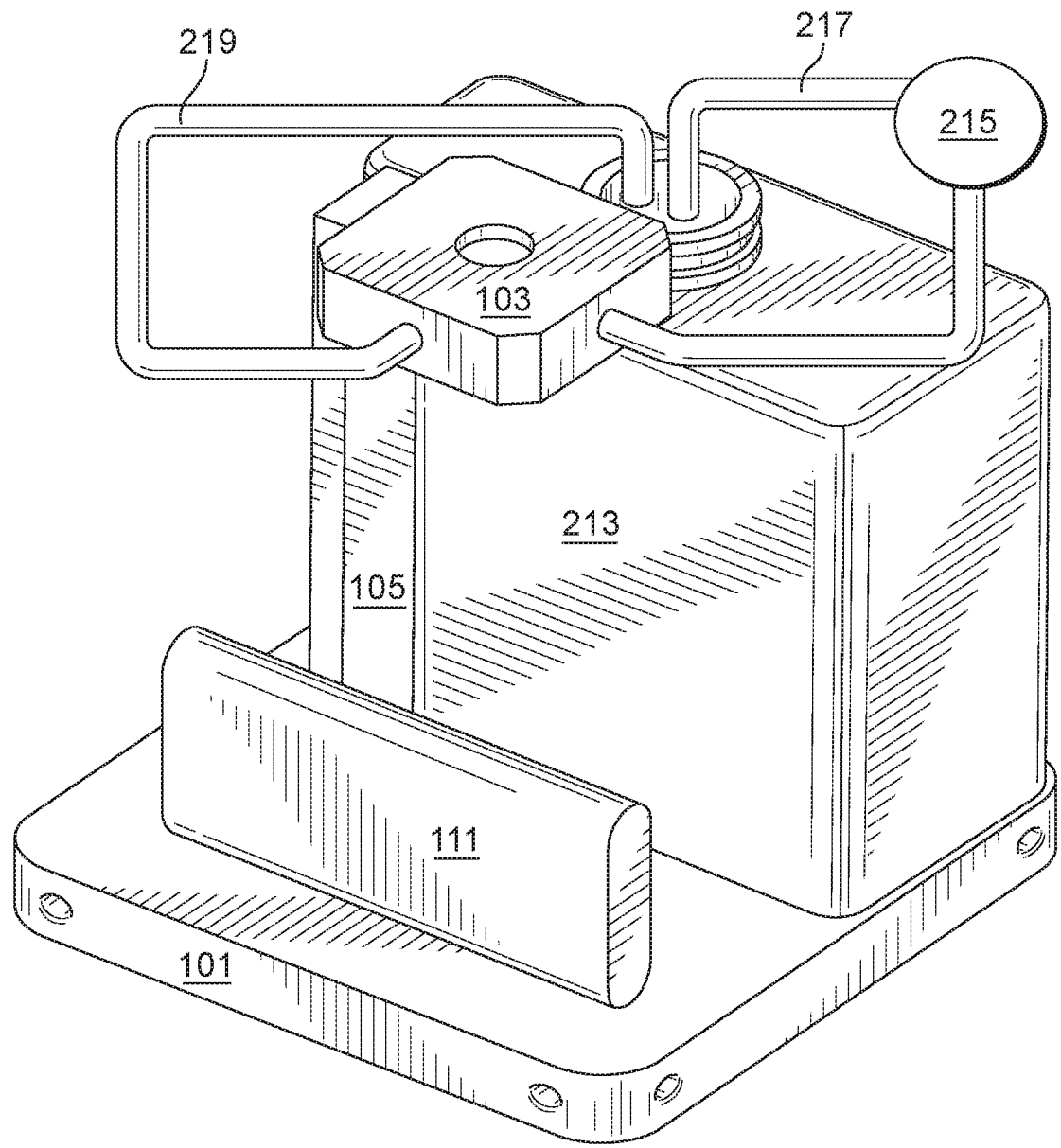
FIG. 3 is a perspective view of a portion of an embodiment of a system in accordance with this disclosure, showing a cooling system.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIGS. 2 and 3. The systems and methods described herein can be used to dramatically speed up and simplify power testing for additive manufacturing machines.

In accordance with at least one aspect of this disclosure, referring to FIGS. 1 and 2, a contained radiation power metering system 100 for measuring power of a radiation source (e.g., a laser) of an additive manufacturing machine (e.g., a powder bed fusion machine) includes a base 101 configured to fit within the additive manufacturing machine (not shown). Any suitable additive manufacturing machine is contemplated herein.

In certain embodiments, the base 101 can be a cartridge plate and/or can be configured to removably fit onto a build plate mount (where a build plate connects to) in the additive manufacturing machine. The base 101 can include any suitable shape, size, and/or other features (e.g. fastener holes 101a, one or more recesses 101b, ridges, or the like) to fit and/or be retained within one or more additive manufacturing machines (e.g., in one or more predetermined position). In certain embodiments, the base 101 can be configured to fit between a build plate and a powder bed of an additive manufacturing system and can be configured to bolt to the additive manufacturing machine.

The system 100 includes a radiation sensor 103 connected to the base 101 and configured to receive radiation from the radiation source and output a radiation power signal (e.g., as a function of the strength of the radiation source). The radiation sensor 103 can be mounted to the base 101 on a post 105 and can be positioned relative to the base 101 for focal length and/or centering position of the radiation source (e.g., so that no adjustment is needed when the base 101 is placed within the additive manufacturing machine). The radiation sensor 103 can be a laser power sensor and/or any other suitable sensor for any suitable radiation source (e.g., an SLS laser, employed radiation source such as fiber laser).

The system 100 includes a wireless module 107 disposed on the base 101 configured to receive the radiation power signal (e.g., either directly or indirectly and in any suitable format) and transmit the radiation power signal from the system 100 to a separate wireless receiver (e.g., associated with a suitable computing device for reading and/or interpreting the radiation power signal for display to a user). The wireless module 107 can include any suitable hardware and/or software as appreciated by those having ordinary skill in the art. The wireless module 107 can be positioned under the radiation sensor 103, e.g., as shown, or in any other suitable position.

In certain embodiments, the system 100 can include an input adapter 109 operatively connected to the radiation sensor 103 to receive the radiation power signal. The input adapter 109 can convert the radiation power signal from a first format (e.g., analog) to second format (e.g., digital) so that the radiation power signal and/or any other suitable data/signals can be operable with the wireless module 107 to be transmitted by the wireless module 107. The input adapter 109 can include any suitable hardware and/or software as appreciated by those having ordinary skill in the art. The input adapter 109 can be positioned under the radiation sensor 103, e.g., as shown, or in any other suitable position.

A battery 111 can be disposed on the base and can be in electrical communication with the wireless module 107 and/or the radiation sensor 103 (if it requires power for example) and/or the input adapter 109. The battery 111 can be positioned under the radiation sensor 103, e.g., as shown, or in any other suitable position. Any other suitable power supply is contemplated herein such that the system 100 can be contained within the additive manufacturing machine without external power (e.g., such that a machine can be sealed an inerted).

In certain embodiments, referring to FIG. 3, the system 100 can include a cooling system 200 (e.g., a liquid cooling system) operatively connected to the radiation sensor 103 to cool the radiation sensor 103. The cooling system 200 can include a coolant tank 213 mounted to the base 101, for example, or any other suitable location.

The cooling system 200 can include a pump 215 configured to pump coolant to the radiation sensor 103. The radiation sensor 103 can be fluidly connected to the coolant tank 213 via one or more coolant lines 217, 219. The one or more coolant lines 217, 219 can include a pump line 217 and a return line 219 which returns coolant to the tank 213. In certain embodiments, the radiation sensor 103 can include a housing, e.g., as shown with an internal volume configured to receive coolant. Any other suitable coolant system is contemplated herein such that the system 100 can be contained within the additive manufacturing machine without external coolant lines (e.g., such that a machine can be sealed an inerted).

It is contemplated that any suitable portion of the system 100 can be mounted to the base 101 in any suitable manner (e.g., fixedly, removably, resting thereon) and/or using any suitable structure (e.g., rested in and or held by brackets attached to the base 101, attached with an adhesive). Any suitable relative arrangement of the portions of the system 100 on the base 101 is contemplated herein.

In accordance with at least one aspect of this disclosure, a method for measuring the power of a radiation source of an additive manufacturing machine can include inserting a contained radiation power metering system into the machine, sealing the contained radiation power metering system in the machine, irradiating a radiation sensor of the contained radiation power metering system with the radiation source, and transmitting a wireless signal from the contained radiation power metering system within the machine to provide a reading of power of the radiation source. The additive manufacturing machine can be a powder bed fusion machine or any other suitable additive manufacturing machine.

As will be appreciated by those skilled in the art, aspects of the present disclosure may be embodied as a system, method or computer program product. Accordingly, aspects of the this disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the this disclosure are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

As appreciated by those having skill in the art, certain additive manufacturing systems (e.g., laser sintering) require periodic power checks and verifications of performance to certify parts manufactured. Embodiments include a self-contained power metering system. Certain embodiments provide wireless data transfer, liquid cooling, and a power meter, all built into a self-contained build module that passes into the inert chamber while maintaining inert seals and all safety interlocks. Embodiments save about 1 hour of setup time, and 1 hour of machine inerting recovery time per power check.

Embodiments resolve many issues with current power meter systems, as well as operates within the machine architecture to preserve integrity of inert atmosphere and works with the existing machine interlocks to maintain operator safety. Embodiments also substantially streamline the power measurement process and drastically reduce the time involved down to less than 5 minutes. Embodiments include a self-contained, battery powered module, on a standalone plate adapter, with wireless transmitter, power source, and fixturing to position the power meter in the correct position and enables automated loading and unloading with zero interlocks bypassed. Embodiments allow power measurement of the laser within the build chamber, while maintaining inert of a powder bed fusion system, for example. Embodiments also precisely position the power meter automatically, without the operator having to reach in through glove box.

The methods and systems of the present disclosure, as described above and shown in the drawings, provide for power meters with superior properties. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A contained radiation power metering system for measuring power of a radiation source of an additive manufacturing machine, comprising:
a base configured to fit within the additive manufacturing machine;
a radiation sensor connected to the base and configured to directly receive radiation from the radiation source and output a radiation power signal; and
a wireless module disposed on the base configured to receive the radiation power signal and transmit the radiation power signal from the system to a separate wireless receiver, wherein the base, the radiation sensor, and the wireless module form a self-contained power metering system configured to pass through one or more seals and/or interlocks into an inert chamber of the additive manufacturing machine while maintaining the inert character of the chamber, wherein the base is configured to fit between a build plate and a powder bed of an additive manufacturing system and is configured to bolt to the additive manufacturing machine.

2. The system of claim 1, further comprising an input adapter operatively connected to the radiation sensor to receive the radiation power signal for converting the radiation power signal from a first format to second format operable with the wireless module.

3. The system of claim 1, further comprising a battery disposed on the base and in electrical communication with the wireless module and/or the radiation sensor.

4. The system of claim 3, wherein the base is a cartridge plate and is configured to removably fit onto a build plate mount in the additive manufacturing machine.

5. The system of claim 4, wherein the radiation sensor is mounted to the base on a post and is positioned relative to the base for focal length and centering position of the radiation source.

6. The system of claim 1, further comprising a cooling system operatively connected to the radiation sensor to cool the radiation sensor.

7. The system of claim 6, wherein the cooling system includes a coolant tank mounted to the base.

8. The system of claim 7, wherein the cooling system includes a pump configured to pump coolant to the radiation sensor.

9. The system of claim 8, wherein the radiation sensor is fluidly connected to the coolant tank via one or more coolant lines.

10. The system of claim 9, wherein the one or more coolant lines includes a pump line and a return line.

11. The system of claim 10, wherein the radiation sensor includes a housing with an internal volume configured to receive coolant.

12. The system of claim 1, wherein the radiation sensor is laser power sensor.

13. A method for measuring the power of a radiation source of an additive manufacturing machine, comprising:
    inserting a contained radiation power metering system into the machine;
    sealing the contained radiation power metering system in the machine such that the contained radiation power metering system passes through one or more seals and/or interlocks into an inert chamber of the additive manufacturing machine while maintaining the inert character of the chamber;
    irradiating a radiation sensor of the contained radiation power metering system with the radiation source; and
    transmitting a wireless signal from the contained radiation power metering system within the machine to provide a reading of power of the radiation source,
    wherein the radiation sensor is configured to directly receive radiation from the radiation source, wherein a base of the contained radiation power metering system is configured to fit between a build plate and a powder bed of an additive manufacturing system and is configured to bolt to the additive manufacturing machine.

14. The method of claim 13, wherein the additive manufacturing machine is a powder bed fusion machine.

15. A contained radiation power metering system for measuring power of a radiation source of an additive manufacturing machine, comprising:
    a base configured to fit within the additive manufacturing machine;
    a radiation sensor connected to the base and configured to receive radiation from the radiation source and output a radiation power signal; and
    a wireless module disposed on the base configured to receive the radiation power signal and transmit the radiation power signal from the system to a separate wireless receiver, wherein the base, the radiation sensor, and the wireless module form a self-contained power metering system configured to pass through one or more seals and/or interlocks into an inert chamber of the additive manufacturing machine while maintaining the inert character of the chamber, wherein the base is configured to fit between a build plate and a powder bed of an additive manufacturing system and is configured to bolt to the additive manufacturing machine.

16. The system of claim 15, further comprising a battery disposed on the base and in electrical communication with the wireless module and/or the radiation sensor.

17. The system of claim 16, wherein the radiation sensor is configured to directly receive radiation from the radiation source.

18. The system of claim 15, wherein the base is a cartridge plate and is configured to removably fit onto a build plate mount in the additive manufacturing machine.

19. The system of claim 15, further comprising, at least one of a battery disposed on the base and in electrical communication with the wireless module and/or the radiation sensor, and/or a cooling system operatively connected to the radiation sensor to cool the radiation sensor.

20. A contained radiation power metering system for measuring power of a radiation source of an additive manufacturing machine, comprising:
    a base configured to fit within the additive manufacturing machine;
    a radiation sensor connected to the base and configured to receive radiation from the radiation source and output a radiation power signal;
    a wireless module disposed on the base configured to receive the radiation power signal and transmit the radiation power signal from the system to a separate wireless receiver;
    at least one of:
        a battery disposed on the base and in electrical communication with the wireless module and/or the radiation sensor; or
        a cooling system operatively connected to the radiation sensor to cool the radiation sensor,
    wherein the base is configured to fit between a build plate and a powder bed of an additive manufacturing system and is configured to bolt to the additive manufacturing machine.

* * * * *